United States Patent [19]

Kober et al.

[11] Patent Number: 5,268,517
[45] Date of Patent: Dec. 7, 1993

[54] STEREOSELECTIVE PREPARATION OF Z-1,2-DIARYLALLYL CHLORIDES AND THE CONVERSION THEREOF INTO AZOLYLMETHYLOXIRANES, AND NOVEL INTERMEDIATES

[75] Inventors: Reiner Kober; Rainer Seele, both of Fussgoenheim; Heinz Isak, Mutterstadt; Eckhard Hichmann, Dannstadt-Schauernheim; Norbert Goetz, Worms; Thomas Zierke, Boehl-Iggelheim, all of Fed. Rep. of Germany

[73] Assignee: BASF Aktiengesellschaft, Ludwigshafen, Fed. Rep. of Germany

[21] Appl. No.: 987,078

[22] Filed: Dec. 7, 1992

Related U.S. Application Data

[63] Continuation of Ser. No. 729,831, Jul. 11, 1991, abandoned, which is a continuation of Ser. No. 547,188, Jul. 3, 1990, abandoned.

[30] Foreign Application Priority Data

Jul. 14, 1989 [DE] Fed. Rep. of Germany ....... 3923674
Nov. 4, 1989 [DE] Fed. Rep. of Germany ....... 3936823

[51] Int. Cl.$^5$ .............................................. C07C 17/24
[52] U.S. Cl. ..................................... 570/193; 570/144; 570/192
[58] Field of Search ........................ 570/193, 192, 144

[56] References Cited

U.S. PATENT DOCUMENTS

| | | | |
|---|---|---|---|
| 3,422,153 | 3/1990 | Mills et al. ............... | 260/612 |
| 4,013,643 | 3/1977 | Nysted ...................... | 260/240 K |
| 4,104,399 | 8/1978 | Pommer et al. ......... | 424/269 |
| 4,464,381 | 8/1984 | Janssen et al. ........... | 424/269 |
| 4,906,652 | 3/1990 | Karbach et al. ......... | 514/318 |

FOREIGN PATENT DOCUMENTS 1204117 5/1986 Canada .
2146987 5/1985 United Kingdom .

OTHER PUBLICATIONS

Ho et al., "Elimination Reactions in the 1,2-Diphenyl-2-Propyl System", *Tetrahedron*, vol. 26, pp. 4277–4286, 1970.

Streitwieser et al., *Introduction to Organic Chemistry*, pp. 563–564, 1970.

Morrison and Boyd, *Organic Chemistry*, pp. 281, 486–487, 318–319, (1983).

The Merck Index of Chemicals and Drugs, 7th edition pp. 6–7, (1960).

Primary Examiner—Marianne M. Cintins
Assistant Examiner—Margaret J. Page
Attorney, Agent, or Firm—Keil & Weinkauf

[57] ABSTRACT

The preparation of Z-1,2-diarylallyl chlorides of the general formula I

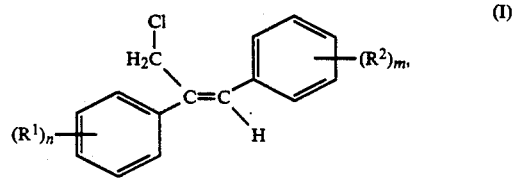

in which $R^1$ and $R^2$, independently of one another, are hydrogen, halogen, alkyl, haloalkyl, alkoxy, haloalkoxy or a substituted aromatic radical, and n and m are 1, 2 or 3, by dehydrating chlorohydrins of the formula II

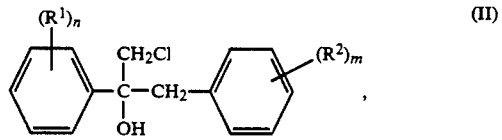

in which the radicals are as defined above, at up to 50° C. in an inert ether or carboxylic acid ester as solvent and in the presence of a carboxylic anhydride and an organic or inorganic acid, the conversion thereof into azolylmethyloxiranes, and novel intermediates are described.

8 Claims, No Drawings

STEREOSELECTIVE PREPARATION OF Z-1,2-DIARYLALLYL CHLORIDES AND THE CONVERSION THEREOF INTO AZOLYLMETHYLOXIRANES, AND NOVEL INTERMEDIATES

This application is a continuation of application Ser. No. 07/729,831 now abandoned, filed on Jul. 11, 1991, which is a continuation of Ser. No. 07/547,188, filed Jul. 3, 1990 now abandoned.

The present invention relates to the stereo-selective preparation of Z-1,2-diarylallyl chlorides of the general formula I

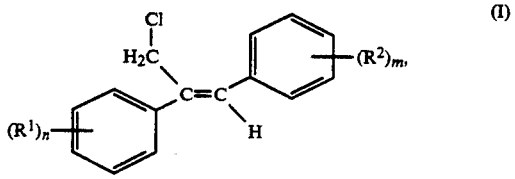

in which $R^1$ and $R^2$, independently of one another, are hydrogen, halogen, alkyl, haloalkyl, alkoxy, haloalkoxy or an unsubstituted or substituted aromatic radical, and n and m are 1, 2 or 3.

The present invention furthermore relates to the conversion of Z-1,2-diarylallyl chlorides into the azolylmethyloxiranes of the formula IV

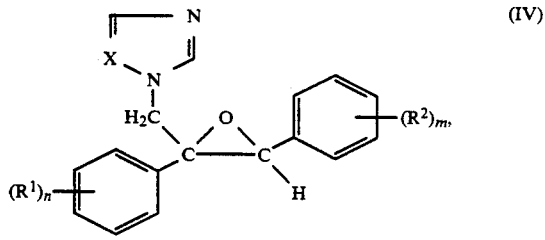

in which $(R^1)_n$, $(R^2)_m$ are as defined above, and X is CH or N.

The present invention also relates to the novel intermediates I and to the epoxidation products V which are precursors thereto.

German Laid-Open Applications DE-OS 3,218,129 and 3,218,130, EP-A 196,038 and U.S. Pat. No. 3,422,153 indicate that compounds of the structural type I are useful intermediates for the preparation of pharmacological, fungicidal and antimycotic active compounds. They have hitherto been obtained free-radical halogenation of corresponding diarylpropene compounds (DE-A 3,218,129 or EP-A 196,038) or by oxidation and subsequent substitution (DE-A 3,218,130). Disadvantages in the methods of the prior art are the use of expensive reagents, for example expensive halogenating reagents such as N-bromosuccinimide for the free-radical bromination, the number of synthetic steps and, in particular, the low stereoselectivity.

It is generally known that molecules which have a specific biological or pharmacological action must in many cases have defined geometrical arrangements of certain functional groups. In the case of the fungicidal active compounds of the general formulae III and IV (see DE-A 2,652,313), it is in particular the Z-configured compounds (cf. the Cahn, Ingold and Prelog sequence rule), i.e. the compounds in which the substituted or unsubstituted phenyl radicals are in the trans position to one another, which have particularly high activity as crop protection agents.

It is therefore an object of the present invention to find a process by which the intermediates I can be prepared in high isomeric purity, i.e. with a high preference for the Z- or trans-configuration of the phenyl radicals on the double bond, and in high yield. It is a further object of the present invention to find a preparation process for the fungicidal azolylmethyloxirane IV which uses advantageous intermediates and is distinguished by high overall yields and by a number of reaction steps which is low compared with the processes described in DE-A 3,218,129 and 3,218,130.

According to the prior art, aryl-substituted alcohols can be converted into the corresponding aryl-substituted olefins or styrenes under acid reaction conditions, for example using sulfuric acid in an organic phase (see, for example, Houben-Weyl, Methoden der organischen Chemie, 4th edition, Volume 5/1b - alkenes, cycloalkenes, arylalkenes, Georg Thieme Verlag, Stuttgart, 1972, pp. 62 ff., in particular pp. 70 and 71; Tetrahedron, 26, (1970) 4277ff.

It is also known that reactions of this type can be carried out with the aid of water-absorbing reagents, for example acetic anhydride. However, relatively high reaction temperatures are generally necessary for these elimination reactions which are described in the literature. Under such reaction conditions, only inadequate E/Z isomer ratios with respect to the aryl/aryl arrangement are obtained.

We have found that the abovementioned objects are achieved by a process for the stereoselective preparation of Z-1,2-diarylallyl chlorides of the general formula I

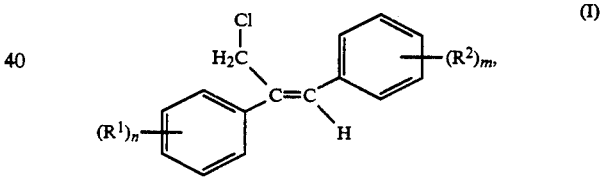

in which $R^1$ and $R^2$, independently of one another, are hydrogen, halogen, alkyl, haloalkyl, alkoxy, haloalkoxy or a substituted aromatic radical, and n and m are 1, 2 or 3, which comprises dehydrating chlorohydrins of the formula II

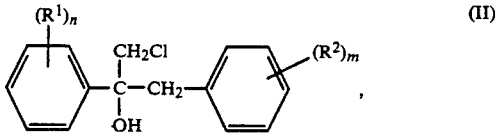

in which the radicals are as defined above, at up to 50° C. in an inert ether or carboxylic acid ester as solvent and in the presence of carboxylic anhydride and an organic or inorganic acid.

The process according to the invention gives Z-configured 1,2-diarylallyl chlorides in high stereo-selectivity. In general and in particular in accordance with the preferred embodiments of the process, the Z:E ratios are from 8:1 to 15:1. The high regioselectivity with which the elimination of water occurs is also surprising, since elimination of water in the direction of the chloromethyl side chain to give chlorovinyldiaryl compounds would have been expected to occur to a greater extent as a side reaction. In addition, expected competing reactions, such as substitution instead of elimination, can successfully be suppressed. The expected acylation of the alcohol function is also virtually absent.

The chlorohydrins of the general formula II are generally known and can be prepared, for example, in accordance with DE-A 2,851,086, EP-A 47,594 or EP-A 15,757 in good yields by the addition reaction of benzyl-Grignard compounds VI with ω-chloroacetophenones VII in accordance with the reaction scheme below:

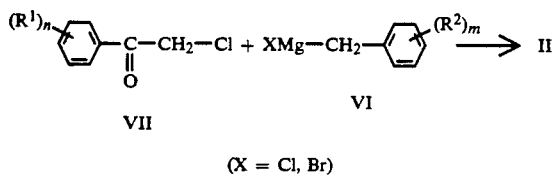

(X = Cl, Br)

In the process for the preparation of the Z-allyl chlorides, it is likewise advantageous to first prepare the chlorohydrins in diethyl ether and to carry out the dehydration as a one-pot process by adding inorganic acid, for example concentrated sulfuric acid, and carboxylic anhydride to the diethyl ether solution at from about −10° to 0° C.

It is also possible, instead of an aqueous workup in the chlorohydrin synthesis, to liberate the chlorohydrin from the magnesium alkoxylate precursor by adding an equimolar amount of an acid, for example sulfuric acid, and subsequently to carry out the dehydration.

It is advantageous and according to the invention here to gradually meter in the carboxylic anhydride, in which case the O-acylation of chlorohydrin can be substantially suppressed compared with the dehydration.

The dehydration according to the invention of the chlorohydrins II is carried out in an ether or ester as solvent. In the case of open-chain ethers, those having at least two oxygen atoms, such as ethers of glycols and low-molecular-weight aliphatic alcohols, for example ethylene glycol dimethyl ether or ethylene glycol diethyl ether, are preferred. Cyclic ethers, such as tetrahydrofuran (THF) and in particular dioxane, are particularly advantageous. Small amounts of aprotic solvents, such as ethyl acetate, halogenated hydrocarbons, such as methylene chloride, or THF, can be added, for example, to dioxane as solvent in order to produce better solvolysis at low temperatures, for example below about 10° C.

Particularly suitable esters for the process according to the invention are those made from low-molecular-weight aliphatic carboxylic acids, in particular monocarboxylic acids, and low-molecular-weight aliphatic alcohols, where the term low-molecular-weight in each case means containing from about 1 to 6 carbon atoms. The following are specific examples of esters: ethyl acetate, ethyl formate, methyl propionate, methyl butyrate, and methyl or ethyl isobutyrate, ethyl acetate being preferred.

The amount of solvent is not particularly crucial and can be varied within broad limits. It is generally from about 1 to 50% by weight, in particular from 2.5 to 10% by weight, based on the chlorohydrin II. A larger excess of solvent is entirely possible, and mixtures of the solvents mentioned, for example, in claims 1 to 5 can also be used for the dehydration, it being possible to vary the mixing ratios in a broad range of from about 10:1 to 1:10. Addition of from 5 to 20% by weight, based on dioxane, have been successful in order to achieve relatively high space-time yields and high Z-product proportions.

The water-absorbing agent added to the reaction mixture is a carboxylic anhydride, in particular an anhydride of an aliphatic low-molecular-weight monocarboxylic acid, such as acetic anhydride, propionic anhydride, butyric anhydride or isobutyric anhydride. However, it is also possible for anhydrides of aliphatic or aromatic dicarboxylic acids, such as malonic anhydride, maleic anhydride, succinic anhydride or phthalic anhydride to be present.

The dehydration is generally carried out using from 0.5 to 3 mole equivalents, in particular from 1 to 2 mole equivalents, of anhydride, based on the chlorohydrin II. Larger amounts are possible, but bring no further advantages.

Particularly advantageous results are obtained using a combination of dioxane and/or THF as solvent with acetic anhydride and sulfuric acid or using ethyl acetate as solvent with isobutyric anhydride and sulfuric acid.

The dehydration is carried out under acidic reaction conditions, using acids which are conventional for this purpose, for example organic sulfonic acids, such as trifluoromethanesulfonic acid, methanesulfonic acid, para-toluenesulfonic acid or naphthalenesulfonic acid and in particular concentrated mineral acids, such as perchloric acid, phosphoric acid and in particular 30 to 99.9%, preferably 50 to 99%, sulfuric acid, or oleum. More carboxylic anhydride is generally used in the case of stronger aqueous acids.

The acid can be employed in a catalytic amount, a stoichiometric amount or in excess, based on II. Amounts of from about 0.01 to 4 mole equivalents, based on II, are preferred. When oleum is used, smaller amounts of from 0.05 to 1 mole equivalents, based on II, are advantageous.

An advantageous variant of the process according to the invention comprises using ketene instead of the carboxylic anhydride as the water-absorbing agent, if desired in combination with a stoichiometric or catalytic amount, based on II, of an aliphatic carboxylic acid. In this case, it is advantageous to initially introduce the carboxylic acid, for example one of the abovementioned low-molecular-weight aliphatic carboxylic acids, and to add the gaseous ketene to the reaction mixture, or to add the gaseous ketene to the chlorohydrin II dissolved in the solvent without addition of carboxylic acid. The amount of ketene here corresponds to the abovementioned amounts for the carboxylic anhydride.

In order to produce a large proportion of the Z isomer, the dehydration should be carried out at the lowest possible temperature, i.e. at up to about 50° C., advantageously at from −25° to +40° C., in particular from −25° to +30° C.

In general, the dehydration is carried out under atmospheric pressure. It is also possible to carry out the reaction under reduced pressure or under super-atmospheric pressure, and in some cases increasing the pressure can result in an increase in the space-time yield.

The Z-1,2-diarylallyl chlorides of the formula I

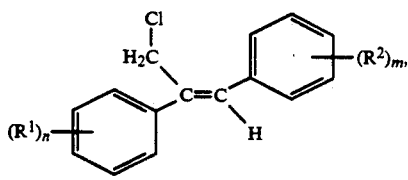

in which $R^1$ and $R^2$, independently of one another, are hydrogen, halogen, $C_1$-$C_7$-alkyl, $C_1$-$C_6$-haloalkyl, $C_1$-$C_5$-alkoxy, $C_1$-$C_5$-haloalkoxy or an aromatic radical which is unsubstituted or monosubstituted to trisubstituted by the radicals mentioned for $R^1$ and $R^2$, and n is 1, 2 or 3, which can be prepared by the process according to the invention, are likewise the subject-matter of the invention.

In the formula I, the indices m and n are preferably 1, and the substituents $R^1$ and $R^2$, independently of one another, are in particular:

hydrogen;

halogen, such as fluorine, chlorine, bromine or iodine, preferably chlorine or fluorine;

linear or branched $C_1$-$C_7$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl;

$C_1$-$C_6$-haloalkyl, such as fluoromethyl, difluoromethyl, trifluoromethyl, chlorodifluoromethyl, dichlorofluoromethyl, trichloromethyl, 1-fluoroethyl, 2-fluoroethyl, 2,2-difluoroethyl, 2,2,2-trifluoroethyl, 2-chloro-2,2-difluoroethyl, 2,2-dichloro-2-fluoroethyl, 2,2,2-trichloroethyl or pentafluoroethyl, preferably trifluoromethyl;

$C_1$-$C_5$-alkoxy, such as methoxy, ethoxy, propoxy, 1-methylethoxy, butoxy, 1-methylpropoxy, 2-methylpropoxy or 1,1-dimethylethoxy, preferably methoxy, ethoxy or propoxy;

$C_1$-$C_5$-haloalkoxy, such as difluoromethoxy, trifluoromethoxy, chlorodifluoromethoxy, dichlorofluoromethoxy, 1-fluoroethoxy, 2-fluoroethoxy, 2,2-difluoroethoxy, 1,1,2,2-tetrafluoroethoxy, 2,2,2-trifluoroethoxy, 2-chloro-1,1,2-trifluoroethoxy or pentafluoroethoxy, preferably trifluoromethoxy;

an aromatic radical, for example phenyl which is unsubstituted or monosubstituted to trisubstituted by a radical $R^3$ which has the preferred meaning given for $R^1$ or $R^2$, i.e. is hydrogen, halogen, linear or branched $C_1$-$C_7$-alkyl, $C_1$-$C_6$-haloalkyl, $C_1$-$C_5$-alkoxy or $C_1$-$C_5$-haloalkoxy.

$R^1$ is preferably 4-F and $R^2$ is preferably 2-Cl.

Z-1,2-diarylallyl chlorides of the general formula I have unexpected advantages over the 1,2-diarylallyl bromides disclosed in DE-A 3,218,129. Besides very simple epoxidation to give the diaryloxiranes of the general formula V, it is particularly advantageous that stereoselective epoxidation means that isomer mixtures of the oxiranes are not obtained, which is the case starting from the known Z-1,2-diarylallyl bromides, but instead oxiranes in which the aryl radicals are transoid are obtained.

Examples of possible substitution patterns are shown in Table 1 below:

TABLE 1

| Compound No. | $(R^1)_n$ | $(R^2)_m$ | Melting pt. [°C.] $^1$H NMR [ppm] |
|---|---|---|---|
| 1.1 | 3-Cl | 3-Cl | |
| 1.2 | 4-Cl | 2,4-diCl | |
| 1.3 | 4-F | 2-CH$_3$ | |
| 1.4 | 4-F | 2-CF$_3$ | |
| 1.5 | H | 2-OCF$_3$ | |
| 1.6 | 4-F | 2-Cl | 66 |
| 1.7 | 4-OCH$_3$ | 2-Cl | |
| 1.8 | 4-Br | 2,4-diCl | |
| 1.9 | 4-C$_6$H$_5$—CH$_2$O | 3-CH$_3$ | |
| 1.10 | 4-p-ClC$_6$H$_4$ | 2-Cl | |
| 1.11 | n-C$_4$H$_9$ | 2-Cl | |
| 1.12 | 4-C$_6$H$_5$ | 2,4-diCl | |
| 1.13 | 4-F | 3-CF$_3$ | |
| 1.14 | 4,5-diCl | 2-CH$_3$ | |
| 1.15 | 4-C$_6$H$_5$O | 2-Cl | |
| 1.16 | 4-Cl | 2-Cl | 79–82 |

In the diarylallyl chlorides I, the Z:E isomer ratio can be determined in a known manner, for example by HPLC (high-pressure liquid chromatography), by gas chromatorgraphy or by $^1$H NMR using the pure Z- and E-isomers as comparison and standardizing the corresponding mixing ratios.

The preparation of the fungicidal active compounds III and IV, starting from the diarylallyl chlorides I or the chlorohydrins II, is shown in the reaction scheme below:

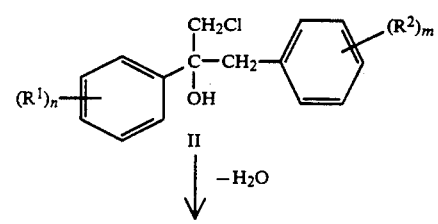

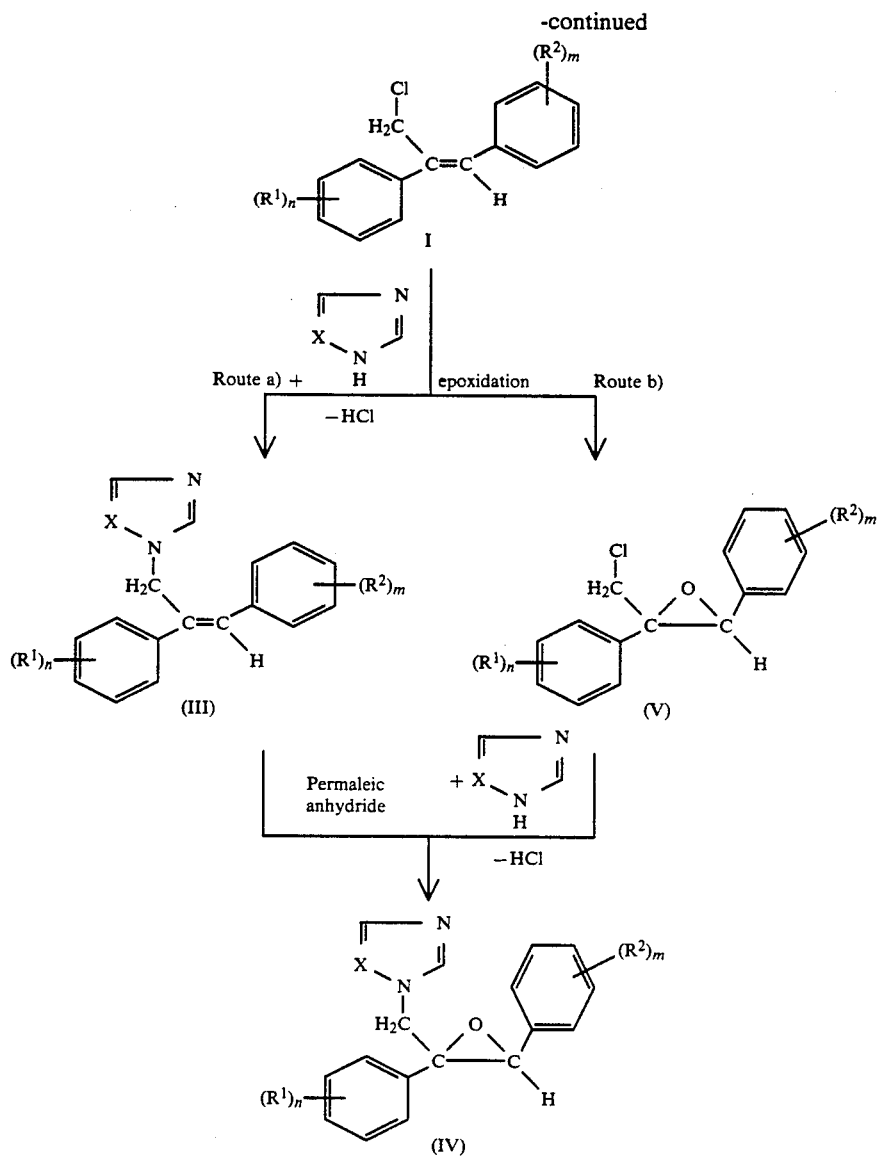

Route b) can be carried out in a conventional manner, for example as described in principle in DE-A 3,218,129. The substitution of the chlorine atom by the azole or imidazole group in compound V is usually carried out in an inert solvent, such as dimethylformamide or N-methylpyrrolidone, in the presence of an inorganic or organic base, for example sodium hydroxide, potassium hydroxide, sodium carbonate, potassium carbonate, dicylohexylamine or dimethylcyclohexylamine.

The intermediates V are novel. With respect to the preferred radicals $R^1$ and $R^2$ and the indices n and m, the definitions given for the compounds I apply analogously. Examples of possible substitution patterns are given in Table 2 below:

TABLE 2

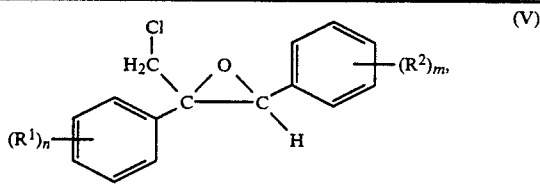
(V)

TABLE 2-continued

| Compound No. | $(R^1)_n$ | $(R^2)_m$ | Melting pt. [°C.] $^1$H NMR [ppm] |
|---|---|---|---|
| 2.1 | 3-Cl | 3-Cl | |
| 2.2 | 4-Cl | 2,4-diCl | |
| 2.3 | 4-F | 2-CH$_3$ | |
| 2.4 | 4-F | 2-CF$_3$ | |
| 2.5 | H | 2-OCF$_3$ | |
| 2.6 | 4-F | 2-Cl | 68-70 |
| 2.7 | 4-OCH$_3$ | 2-Cl | |
| 2.8 | 4-Br | 2,4-diCl | |
| 2.9 | 4-C$_6$H$_5$—CH$_2$O | 3-CH$_3$ | |
| 2.10 | 4-p-ClC$_6$H$_4$ | 2-Cl | |
| 2.11 | n-C$_4$H$_9$ | 2-Cl | |
| 2.12 | 4-C$_6$H$_5$ | 2,4-diCl | |
| 2.13 | 4-F | 3-CF$_3$ | |
| 2.14 | 4,5-diCl | 2-CH$_3$ | |
| 2.15 | 4-C$_6$H$_5$O | 2-Cl | |
| 2.16 | 4-Cl | 2-Cl | |

In route a), the first step, i.e. the substitution, proceeds analogously to the final step of route b). The dehydration and the subsequent substitution can advantageously be carried out in a one-pot process without isolation and purification of the intermediate II.

The epoxidation of the compounds III is carried out according to the invention in the presence of a large excess of permaleic acid, the permaleic acid being prepared in situ by reacting from 5 to 30 mole equivalents, in particular from 5 to 10 mole equivalents, of maleic anhydride, based on III, with less than the stoichiometric amount of hydrogen peroxide solution, based on the maleic anhydride. In general, anhydride:H₂O₂ molar ratios of from 1.5 to 10, in particular from 2 to 4, are employed. A 30 to 50% strength aqueous solution of hydrogen peroxide may advantageously be used.

The reaction temperature for the epoxidation can be from 0° to 100° C., in particular from 20° to 80° C.

The epoxidation is carried out in the presence of an aprotic, polar solvent. Examples of suitable solvents are halogenated hydrocarbons, such as dichloromethane, dichloroethane, chlorobenzene or chlorotoluene, or aromatic hydrocarbons, such as benzene, toluene or xylene. The amount of solvent is not particularly crucial and is generally from 5 to 50% by weight, in particular from 10 to 20% by weight, based on the olefin.

Using this epoxidation method, the azolylmethyloxiranes IV can be obtained in considerably higher yields than in the processes described in DE-A 3,218,129.

The individual synthesis steps are described in the experimental examples below.

EXAMPLE 1

Preparation of the Starting Materials II

1-Chloro-2-(4-chlorophenyl)-3-(2-chlorophenyl)propan-2-ol 5.0 g (0.031 mol) of 2-chlorobenzyl chloride are added within 5 minutes at from 24° to 36° C. to 9.7 g (0.404 mol) of magnesium turnings in 20 ml of absolute ether. After the reaction has commenced, a solution of 200 ml of absolute ether and 50.2 g (0.31 mol) of 2-chlorobenzyl chloride is added dropwise. The mixture is subsequently refluxed for about a further 10 minutes, the excess magnesium is decanted off under nitrogen, and the Grignard solution is cooled to 0° C. 55.7 g (0.3 mol) of para-chloro-ω-chloroacetophenone dissolved in 350 ml of toluene are then added dropwise, and the reaction mixture is stirred at 0° C. for 1.5 hours and added dropwise at from about 2° to 6° C. to 1.5 l of concentrated ammonium chloride solution. Extraction with methyl tert.-butyl ether and subsequent conventional work-up gives 92.9 g (yield 99%, purity according to HPLC: 68.2%) of 1-chloro-2-(4-chlorophenyl)-3-(2-chlorophenyl)propan-2-ol as a crude oil, which can be further reacted directly. For characterization, the product was recrystallized from n-hexane.

Melting point: 64° to 69° C.

EXAMPLES 2 TO 5 AND COMPARISON EXAMPLES I TO IV

Dehydration of the Chlorohydrins II

Z-3-Chloro-2-(4-chlorophenyl)-1-(2-chlorophenyl)propene Compound No. 1.16 in Table 1

24.5 g (0.24 mol) of acetic anhydride are added at −2° C. to 60 g (0.2 mol) of the chlorinated alcohol described in Example 1 in 230 ml of dioxane and 23 ml of tetrahydrofuran, and 2.36 g (0.024 mol) of concentrated sulfuric acid are subsequently added to the mixture. After the mixture has been stirred at 0° C. for 3 hours, HPLC analysis shows that virtually all the starting material has reacted.

A mixture of half-saturated sodium chloride solution and 50% strength sodium hydroxide solution is subsequently added at 0° C. over the course of 30 minutes until the pH is from 8 to 9.

Finally, the organic phase is dried and evaporated under reduced pressure and can be used for subsequent reactions without further purification.

Yield 55.7 g. (Z/E=9.1/1), crude oil, recrystallization from n-hexane to get the pure Z-isomer of melting point 79° to 82° C.

The Z-1,2-diarylallyl chlorides in Table 1 can be prepared in a similar manner.

Z-3-chloro-2-(4-fluorophenyl)-1-(2-chlorophenyl)propene

Example No. 1.6 in Table 1

1-Chloro-2-(4-fluorophenyl)-3-(2-chlorophenyl)-propan-2-ol, prepared by Grignard addition of 2-chlorobenzylmagnesium chloride to para-fluoro-ω-chloroacetophenone and employed as the crude material having an HPLC purity of 78-87%, was reacted as described in Example 2 under the reaction conditions given in Table 2. The proportions of Z- and E-isomers were determined by HPLC (high-pressure liquid chromatography) analysis (uncorrected relative area percentages).

TABLE 2

Dehydration of 1-chloro-2-(4-fluorophenyl)propan-2-ol

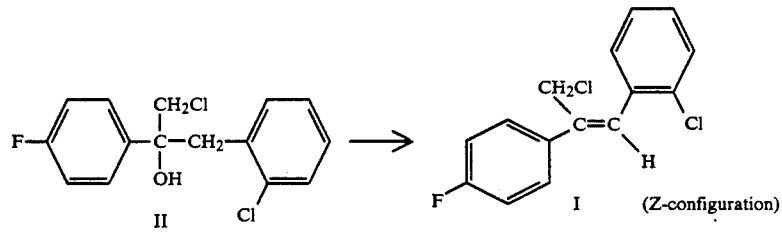

| | Solvent | Acidic Reagents | Amount of II (g/mol) | Temp. (°C.) | Time (min) | Yield of Z-isomer (%) | Z:E ratio | Reference[a] |
|---|---|---|---|---|---|---|---|---|
| Example | | | | | | | | |
| 3 | 20 ml of dioxane 2 ml of THF | 0.2 g of conc. H₂SO₄ 2.3 g of acetic anhydride | 5/0.018 | −2 | 60 | 58 | 9.2 | |
| 4 | 20 ml of dioxane | 0.2 g of conc. H₂SO₄ | 5/0.018 | 25 | 30 | 55 | 6.5 | |

TABLE 2-continued

| | Solvent | Reagent | Ratio | Temp (°C) | Time | Yield | Z:E | Reference |
|---|---|---|---|---|---|---|---|---|
| 5 | 2 ml of THF<br>20 ml of ethyl acetate | 2.3 g of acetic anhydride<br>0.2 g of conc. $H_2SO_4$<br>3 g of isobutyric anhydride | 5/0.018 | 25 | 30 | 50 | 7.7 | |
| Comp. Ex. | | | | | | | | |
| I | 20 ml of dioxane<br>2 ml of THF | 0.2 g of conc. $H_2SO_4$ or<br>2.3 g of acetic anhydride | 5/0.018 | 25 | 60 | no conversion | | [a] |
| II | 20 ml of ethyl acetate<br>2 ml of THF | 0.2 g of conc. $H_2SO_4$<br>2.3 g of acetyl chloride | 5/0.018 | 40 | 30 | 23[b] | 6.8 | Ann. chim. et phys. [11] 6, (1936) 313 |
| III | 50 ml of formic acid | | 10/0.036 | 100 | 50 | 8.3 | 3.8 | J. Am. Chem. Soc. (1938) 2204 and 2208 |
| IV | 50 g of toluene<br>80 ml of cyclohexane | 2 g of p-toluenesulfonic acid | 50/0.18.. | Reflux | 150 | 46.5 | 4.5 | Naturwiss. 44, (1957) 584 |
| V | 15 g of acetonitrile | 75 mg of p-toluenesulfonic acid | $2.1/7.56 \cdot 10^{-3}$ | 50 | 180 | no conversion | | Tetrahedron 26, (1970) 4277–4286 |

[a] in accordance with the literature references given
[b] 19% of starting mixture, 13% acylate formation via the OH function in the chlorohydrin II

EXAMPLE 6

Preparation of the Chlorohydrin and In Situ Dehydration

1-Chloro-2-(4-fluorophenyl)-3-(2-chlorophenyl)propan-2-ol 170 g (1.0 mol) of 2-chlorobenzyl chloride dissolved in 400 ml of diethyl ether were added to 36.0 g (1.5 mol) of magnesium turnings in 200 ml of diethyl ether. 155 g (0.9 mol) of para-fluoro-ω-chloroacetophenone, dissolved in 450 ml of diethyl ether, were subsequently added dropwise at −10° C., and the mixture is then stirred for a further 2 hours at 25° C.

49.0 g (0.5 mol) of concentrated sulfuric acid in 300 ml of diethyl ether are then added dropwise at −10° C. The mixture is allowed to warm to 25° C., and the precipitated salt is filtered off with suction. The crude ether solution of the chlorohydrin is then employed further.

Z-3-chloro-2-(4-fluorophenyl)-1-(2-chlorophenyl)propene 8.0 g (0.08 mol) of concentrated sulfuric acid are added at −10° C. to 525 ml of the above-described crude solution, containing about 134.5 g of chlorohydrin (corresponding to 0.45 mol), and 57.1 g (0.56 mol) of acetic anhydride are subsequently added dropwise over the course of 2 hours. A small amount of precipitated salt is then again filtered off. The solvent is evaporated from the filtrate, and the crude allyl chloride can be used further for the triazole substitution or for the epoxidation.

EXAMPLE 7

Ketene Variant

Z-3-chloro-2-(4-fluorophenyl)-1-(2-chlorophenyl)propene 250 ml of dioxane, 25 ml of tetrahydrofuran, 2.4 g of acetic acid (0.2 mol) and 69 g (0.23 mol) of crude 1-chloro-2-(4-fluorophenyl)-3-(2-chlorophenyl)propan-2-ol obtained from the Grignard reaction as per Example 1 are mixed at 0° C., and 43 g (1.02 mol) of ketene in gaseous form are introduced within about 1 hour. After customary work-up, a virtually identical yield as when acetic anhydride is used in the above-described Example 2 is achieved according to HPLC analysis. The Z:E isomer ratio when the reaction is carried out in this manner is about 11:1.

EXAMPLES 8 AND 9

Preparation of the Azolylmethyloxiranes IV By Route a)

Z-3-(1,2,4-triazol-1-yl)-2-(4-chlorophenyl)-1-(2-chlorophenyl)propene 6.6 g of sodium hydroxide are added to a solution of 11.5 g (0.17 mol) of triazole in 150 ml of dimethylformamide, and the mixture is warmed at about 70° C. until, with stirring, a clear solution has been formed. The mixture is subsequently cooled to 10° C., and 49.5 g of the Z-3-chloro-2-(4-chlorophenyl)-1-(2-chlorophenyl)propene as the crude product, prepared as in Example 2, dissolved in 50 ml of dimethylformamide, are added dropwise within hour, and the mixture is then stirred at room temperature for a further 4 hours.

200 ml of water are then added, and the mixture is extracted several times with methyl tert.-butyl ether. The combined organic phases are washed, dried and evaporated at a reduced pressure. Recrystallization from methyl tert.-butyl ether and n-hexane gives 24.4 g of Z-3-(1,2,4-triazol-1-yl)-2-(4-chlorophenyl)-1-(2-chlorophenyl)propene of melting point 106°–110° C.

cis-2-(1,2,4-Triazol-1-ylmethyl)-2-(4-fluorophenyl)-3-(2-chlorophenyl)oxirane 84 g (0.9 mol) of maleic anhydride and 6 drops of concentrated sulfuric acid in 90 ml of dichloroethane are warmed to 50° C. with 22 g of 50% strength hydrogen peroxide. 28 g (0.089 mol) of Z-3-(1,2,4-triazol-1-yl)-2-(4-fluorophenyl)-1-(2-chlorophenyl)propene in 75 ml of dichloroethane are added dropwise. The mixture is stirred at this temperature for a further 3 hours and subsequently at 70° C. for a further 2.5 hours.

The reaction mixture is cooled, the precipitated maleic acid is filtered off with suction, and the filtrate is washed by shaking with thiosulfate solution and dilute sodium hydroxide solution. The organic phase is dried, substantially evaporated at about 50° C. under reduced pressure, cooled and re-evaporated to give 14 g of useful product (°50% yield).

EXAMPLES 10 AND 11

Preparation of the Azolylmethyloxiranes IV By Route b)

cis-1-Chloromethyl-2-(2-chlorophenyl)-1-(4-fluorophenyl)oxirane

Compound No. 2.6 in Table 2

56.2 g (0.2 mol) of Z-3-chloro-2-(4-fluorophenyl)-1-(2-chlorophenyl)propene in 530 ml of glacial acetic acid are mixed with 196 g (2 mol) of maleic anhydride, and 68 g (1 mol) of 50% strength hydrogen peroxide solution are added at 25° C. within 1 hour. The mixture is stirred at 40° C. for a further 3 to 4 hours and subsequently at 25° C. for a further 10 hours.

Finally, the reaction mixture is stirred into 3 liters of water and 50 ml of 10% strength sodium thiosulfate solution, and a further small amount of thiosulfate solution is added if necessary until peroxide is no longer detectable. The colorless precipitate produced is filtered off with suction and dried. The crude material is employed without further purification. (Recrystallization of n-hexane; m.p. 68° to 70° C.).

cis-2-(1,2,4-Triazol-1-ylmethyl)-2-(4-fluorophenyl)-3-(2-chlorophenyl)oxirane 1.5 g (5 mmol) of cis-1-chloromethyl-2-(2-chlorophenyl)-1-(4-fluorophenyl)oxirane and 0.69 g (7.5 mmol) of sodium 1,2,4-triazolide are stirred at 75° C. for 5 hours in 7 ml of dimethylformamide. After cooling, the mixture is neutralized by adding a little acetic acid, and a little water (about 10 ml) is added, a crystalline product precipitating (yield: 1.4 g). The product is filtered off with suction, washed with water and dried under reduced pressure.

We claim:

1. A process for the stereoselective preparation of the Z-configuration in preference to the E-configuration of 1,2-diarylally chloride of the formula I

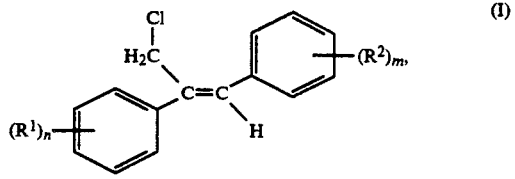

in which $R^1$ and $R^2$ represent halogen, and m and n are 1, 2, or 3, which process comprises dehydrating a chlorohydrin of the formula II

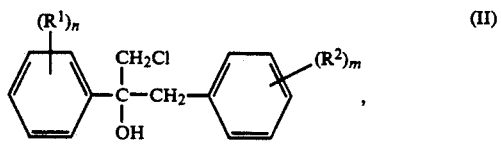

in which $R^1$, and $R^2$, m and n are as defined above, at from $-25°$ to $50°$ C. in an inert ether or carboxylic acid ester as solvent and in the presence of a carboxylic anhydride or ketene and an organic or inorganic acid.

2. The process of claim 1, wherein the solvent used is a cyclic ether or a low-molecular-weight aliphatic carboxylic acid ester.

3. The process of claim 1, wherein the dehydration is carried out in the presence of an anhydride of aliphatic monocarboxylic acid.

4. The process of claim 1, wherein the process is carried out in the presence of ketene and an organic or inorganic acid.

5. The process of claim 1, wherein the process is carried out in the presence of ketene in combination with a catalytic to stoichiometric amount of an organic carboxylic acid, based on the chlorohydrin II.

6. The process of claim 1, wherein the dehydration is carried out at from $-25°$ to $+30°$ C.

7. The process of claim 1, wherein the process is carried out in the presence of a carboxylic anhydride and an organic or inorganic acid.

8. The process of claim 1, wherein the ratio of the Z configuration that is formed to the E configuration is from 8:1 to 15:1.

* * * * *

UNITED STATES PATENT AND TRADEMARK OFFICE
CERTIFICATE OF CORRECTION

PATENT NO. : 5,268,517
DATED : Dec. 7, 1993
INVENTOR(S) : KOBER et al.

It is certified that error appears in the above-identified patent and that said Letters Patent is hereby corrected as shown below:

On the title page, Item [75]:
<u>INVENTORS</u>

"Hichmann" should read --Hickmann--.

Signed and Sealed this

Tenth Day of May, 1994

Attest:

BRUCE LEHMAN

Attesting Officer     Commissioner of Patents and Trademarks